US009050356B2

(12) United States Patent
Cornelli

(10) Patent No.: US 9,050,356 B2
(45) Date of Patent: Jun. 9, 2015

(54) COMPOSITIONS COMPRISING CHITOSAN SUITABLE FOR COMPREHENSIVE THERAPEUTIC TREATMENT OR COMPREHENSIVE PREVENTION OF THE METABOLIC SYNDROME

(75) Inventor: Umberto Cornelli, Milan (IT)

(73) Assignee: Cor. Con. International S.R.L., Parma (IT)

(*) Notice: Subject to any disclaimer, the term of this patent is extended or adjusted under 35 U.S.C. 154(b) by 518 days.

(21) Appl. No.: 12/281,615

(22) PCT Filed: Mar. 2, 2007

(86) PCT No.: PCT/EP2007/052023
§ 371 (c)(1),
(2), (4) Date: Nov. 25, 2008

(87) PCT Pub. No.: WO2007/099170
PCT Pub. Date: Sep. 7, 2007

(65) Prior Publication Data
US 2009/0258839 A1    Oct. 15, 2009

(30) Foreign Application Priority Data

Mar. 3, 2006 (IT) .............................. M12006A0384

(51) Int. Cl.
*A61K 31/722* (2006.01)
*A61P 3/00* (2006.01)
*C08L 5/08* (2006.01)

(52) U.S. Cl.
CPC .... *A61K 31/722* (2013.01); *C08L 5/08* (2013.01)

(58) Field of Classification Search
None
See application file for complete search history.

(56) References Cited

U.S. PATENT DOCUMENTS

| 4,223,023 | A | | 9/1980 | Furda |
| 5,453,282 | A | * | 9/1995 | Kanauchi et al. ............. 424/464 |
| 5,654,001 | A | | 8/1997 | Kanauchi et al. |
| 6,030,953 | A | | 2/2000 | Bailly et al. |
| 6,180,148 | B1 | | 1/2001 | Yajima |
| 2002/0016307 | A1 | * | 2/2002 | Mullins ........................... 514/55 |
| 2003/0069206 | A1 | | 4/2003 | Nichols |

FOREIGN PATENT DOCUMENTS

| CN | 1692782 A | 11/2005 |
| DE | 100 54 450 | 3/2002 |
| JP | 54-148090 A | 11/1979 |
| JP | 4-108734 A | 4/1992 |
| JP | 06-056674 A | 3/1994 |
| JP | 2000245373 A | 9/2000 |
| JP | 2002-275073 A | 9/2002 |
| JP | 2003-113089 A | 4/2003 |
| JP | 2003-238602 A | 8/2003 |
| RU | 2290185 C1 | 12/2006 |
| WO | WO 2004/084636 A1 | 10/2004 |
| WO | WO 2004/100681 A1 | 11/2004 |
| WO | WO 2005/089731 A2 | 9/2005 |

OTHER PUBLICATIONS

Groop. British Journal of Nutrition, (2000) 83; Suppl. 1, S39-S48.*
L112, User Information, www.l112.com, Internet Archive Feb. 13, 2002.*
Bondiolotti et al. European Journal of Pharmacology 567 (2007) 155-158.*
Deen, American Family Physician, vol. 69, No. 12, Jun. 15, 2004.*
Definition of "treatment," downloaded from the internet Apr. 8, 2013.*
Definition of "ameliorate," downloaded from the internet Apr. 8, 2013.*
The Healthy Life, How Chitosan Can Help You Lose Weight and Lower Your Cholesterol, May 2, 2001, http://www.thehealthierlife.co.uk/natural-health-articles/weight-loss/chitosan-lose-weight-lower-cholesterol-00990/.*
Fillippatos et al. Current Medical Research and Opinion, vol. 21, No. 12, Dec. 2005, pp. 1997-2006, abstract only.*
Gou, G. et al., Method for producing yoghurt table with blood pressure lowering effect, *Database Chemabs (Online)*, Chemical Abstracts Service, Columbus OH; Jul. 17, 2006, XP002434489.
Artyukov, A. et al., Composition for normalization of lipid metabolism and reducing body mass and method for its preparation, *Database WPI Week 0726*, Dec. 27, 2006, XP002435622.
Abbassy, A., Update Management of Obese Diabetics, retrieved on May 21, 2007, from the Internet: URL: http://www.emro.who.int/ncd/Presentations/Leb0504/Day1/Dr%20Abbasay.ppt, XP002434488.
Deedwania, P.C. and Volkova, N. 2005 "Current treatment options for the metabolic syndrome" *Current Treatment Options in Cardiovascular Medicine* 7:61-74.
Sciutto, A.M. and Colombo, P. 1995 "Lipid-lowering effect of chitosan dietary integrator and hypocaloric diet in obese subjects" *Acta Toxicol Ther* 16:215-230.
Basic Egg Pasta Recipe. Available online at www.yumyum.com on Feb. 1, 2001.
RecipeSource Miscellaneous Hints and Helpful Information Flour Weights. Available online at www.recipesource.com on Feb. 1, 2002.
Kanauchi, O. et al., 1994, "Increasing Effect of a Chitosan and Ascorbic Acid Mixture on Fecal Dietary Fat Excretion," *Biosci Biotech Biochem* 58: 1617-1620.
Kanauchi, O. et al., 1995, "Mechanism for the Inhibition of Fat Digestion by Chitosan and for the Synergistic Effect of Ascorbate," *Biosci Biotech Biochem* 59: 786-790.
Kanai, Satoshi, 1996, "Food Material That Does Not Make You Fat Even if You Eat a Lot?" *Chemistry and Biology*, 34: 553-557.

* cited by examiner

*Primary Examiner* — Layla Bland
(74) *Attorney, Agent, or Firm* — LeClairRyan, a Professional Corporation

(57) ABSTRACT

The present invention relates to compositions comprising chitosan, in the form of drugs or food supplements, suitable for comprehensive therapeutic treatment or comprehensive prevention of the metabolic syndrome. Also described is their preparation. More generally, the invention concerns the use of chitosan for comprehensive therapeutic treatment or comprehensive prevention of the metabolic syndrome.

10 Claims, No Drawings

COMPOSITIONS COMPRISING CHITOSAN SUITABLE FOR COMPREHENSIVE THERAPEUTIC TREATMENT OR COMPREHENSIVE PREVENTION OF THE METABOLIC SYNDROME

This application is U.S. National Phase of International Application PCT/EP2007/052023, filed Mar. 2, 2007 designating the U.S., and published in English as WO 2007/099170 on Sep. 7, 2007, which claims priority to Italian Patent Application No. MI2006A000384 filed Mar. 3, 2006.

FIELD OF THE INVENTION

The present invention relates to compositions comprising chitosan, in the form of a drug or food supplement, suitable for the comprehensive therapeutic treatment or comprehensive prevention of the metabolic syndrome.

PRIOR ART

Over the last 20 years, the ever growing incidence of cardiovascular diseases and type II diabetes variously linked with pathologies such as dyslipidemia, glucose intolerance, hypertension and overweight, have led to the identification of a possible common cause of all these pathologies, in addition to the food hygiene component dietary element which seemed the most obvious cause, and this has prompted all the aforesaid symptoms to be combined into a "syndrome". The common cause of the thus defined syndrome was initially identified as being insulin resistance (Reaven G M, Banting lecture, 1988: Role of insulin resistance in human disease, Diabetes 1988; 37:1595-1607).

Various names have been proposed for the new syndrome, such as syndrome X, Reaven's syndrome (the first person to identify insulin resistance), metabolic, multiple metabolic, plurimetabolic, dysmetabolic, cardiovascular dysmetabolic and cardiometabolic syndrome, or, without the term syndrome, naming it "H phenomenon" or even "deadly quartet". Differences in its name still exist. However, a tacit accord exists in defining this pathological association as "the metabolic syndrome".

Since 1998, WHO has proposed various principal characteristics for diagnosing patients with the metabolic syndrome (Alberti et al, Definition, diagnosis and classification of diabetes mellitus and its complications. Part 1: diagnosis and classification of diabetes mellitus: provisional report of a WHO consultation. Diabetes Med. 1998: 15: 539-553).

In 2005, the National Cholesterol Education Programs Adult Treatment Panel III Report (ATP III), re-proposed the metabolic syndrome classification with an outcome much more linked to its prevention (Grundy S M et al. Diagnosis and management of the Metabolic Syndrome. An American Heart Association/National Heart, Lung, and Blood Institute scientific statement. Circulation 2005; 112: e285-290). Other classifications exist, such as AACE (American Association of Clinical Endocrinologists), EGIR (European Group Study Insulin Resistance) and IDF (International Diabetes Foundation), which are essentially based on the same parameters with the only differences being in the maximum or minimum values for evaluating said parameters. This classification of the metabolic syndrome (hereinafter indicated as MS) is referred to in the following text as ATP III 2005. The diagnostic parameters referred to are very simple and easily identifiable in order to facilitate the diagnosis and prevention of MS and its subsequent cardiovascular and/or endocrine implications; however, there remains an absence of therapy which deals with MS in its entirety.

Even today the suggested therapy is in fact to treat the individual pathologies with single specific therapies, i.e. separately treating hypertension, dyslipidemia, excess body weight etc, in that each of these is accompanied by a risk of serious pathology (cardiovascular diseases, type II diabetes etc.)

Many methods and compounds have been proposed as therapy for the individual pathologies, including chitosan, which has been proposed for reducing body weight and cholesterol levels (Singla A K et al.: Some pharmaceutical and biological aspects—an update. Journal of Pharmacy and Pharmacology, 2000; 53. 1047-1067 and Schiller et al. A randomized, double blind, placebo controlled study examining the effect of a rapidly soluble chitosan dietary supplement on weight loss and body composition in overweight and mildly obese individuals. JANA 2001; 4: 42-49).

A tentative therapy has been proposed for MS using oral hypoglycemics (thiazolidenediones or metformin), the activities of which are awaiting confirmation. They are, however, targeted at alterations in glycemia and insulin sensitivity alone, these being pathologies which represent only a part of MS.

Therefore, the problem is of comprehensively treating the pathologies involved in the metabolic syndrome with a single therapy.

SUMMARY

The present invention relates to compositions comprising chitosan, in the form of a drug or food supplement, which are suitable for comprehensive therapeutic treatment or comprehensive prevention of the metabolic syndrome. Also described is their preparation.

More generally, the invention concerns the use of chitosan for comprehensive therapeutic treatment or comprehensive prevention of the metabolic syndrome.

DETAILED DESCRIPTION OF THE INVENTION

The terms given in the present description have the following meanings:

The metabolic syndrome (MS)—an association of pathologies, which are diagnosed together according to the ATP III 2005 classification, and possibly attributable to a single aetiological cause.

ATP III 2005—Classification for diagnosing if a patient suffers from MS. To be classified as MS at least three of the following parameters must be positively assessed in the patient:
a) Waist circumference equal to or greater than 102 cm in men and equal to or greater than 88 cm in women
b) Triglyceride level equal to or greater than 150 mg/dL
c) HDL cholesterol level less than 40 mg/dL in men and less than 50 mg/dL in women
d) Arterial blood pressure equal to or greater than 130/85 mm Hg
e) High basal fasting glucose equal to or greater than 100 mg/dL, or altered glucose load curve.

The present invention relates to compositions, comprising chitosan, in the form of a drug or food supplement, suitable for comprehensive therapeutic treatment or comprehensive prevention of the metabolic syndrome (MS).

It has been surprisingly found that pharmaceutical compositions or food supplements can be prepared which are suitable for comprehensive therapeutic treatment or comprehensive prevention of MS pathologies, classified in accordance with ATP III 2005 criteria.

In particular chitosan has been found to induce a reduction in basal glucose levels to less than 110 mg/dL, as well as a reduction in arterial blood pressure to less than 130/85 mm Hg.

The present compositions can also contain, in addition to chitosan, lubricants, such as magnesium stearate, and other excipients such as tartaric acid and/or adjuvants and/or flavourings. Optionally the compositions can also contain other antioxidants.

The compositions of the present invention also preferably comprise ascorbic acid in a quantity between 1% and 10% by weight on the chitosan present, and even more preferably between 4% and 8% by weight.

The compositions can be prepared in any pharmaceutically acceptable form, of which the tablet form is preferred, but any administration means is possible and can be considered.

The quantity of chitosan in the compositions is variable and depends on dosage: preferably the unit doses contain chitosan in quantities between 0.1 g and 1.5 g, more preferably between 0.25 g and 1 g and even more preferably between 400 and 600 mg.

A further aspect of the present invention is a process for preparing a pharmaceutical composition or a food supplement, suitable for comprehensive therapeutic treatment or comprehensive prevention of the metabolic syndrome, by means of blending chitosan with suitable excipients or diluents or with suitable substances having complementary activity. All known methods for preparing the various compounds in drugs or food supplements by means of blending can be used. Methods for preparing tablets, in particular tablets containing ascorbic acid and magnesium stearate, are preferred.

A further aspect of this invention concerns the use of chitosan for preparing a drug or a food supplement suitable for comprehensive therapeutic treatment or comprehensive prevention of the metabolic syndrome. In particular, the use of chitosan enables basal glucose levels to be reduced to less than 110 mg/dL and arterial blood pressure to be reduced to less than 130/85 mm Hg, as well as body weight and cholesterol levels to be reduced.

EXAMPLES

Example 1

Clinical Studies to Evaluate the Effect of a Tablet Containing Chitosan on the Pathologies that Making up the Metabolic Syndrome 70 subjects aged between 20 and 75 years were enrolled. The admission criteria required them to satisfy the following parameters: a body mass index (BMI) >25 kg/m$^2$ and total cholesterol levels >150 mg/dL.

All the enrolled subjects attended the experimental centre at Spoltore/San Valentino (PE) and were examined for the necessary clinical parameters by the centre researchers. The subjects were asked to maintain constancy in their food intake and physical activity, enabling the action of the therapy under study to be evaluated in the best manner. All subjects were subjected to hematological and hematochemical investigations before and at the end (after three months) of the treatment under study. For the laboratory assessments, fasting in the 12 hours preceding blood withdrawal was requested. Blood was taken from the brachial vein into suitable heparinized tubes, which were subsequently centrifuged to isolate the plasma on which to carry out the laboratory assessments. All tests were implemented within four hours of withdrawing blood, which was maintained on ice until the assessment.

64 out of the 70 enrolled subjects completed the trial. The six missing cases did not attend monthly visits to collect the product and were therefore excluded from the calculation of results. Table 1 describes the general characteristics of the enrolled patients who completed the treatment.

TABLE 1

General characteristics of the patients under treatment

| Parameters | yes MS | no MS |
|---|---|---|
| Males | 14 | 19 |
| Females | 13 | 18 |
| Age | 53 ± 10.1 | 50 ± 6.6 |

Average age ± SD (Standard Deviation);
MS = the metabolic syndrome according to ATP III 2005 criteria.

The two patient groups were characterized by the clinical/diagnostic parameters given in table 2

TABLE 2

Parameters considered for diagnostic purposes: averages ± SD

| Parameters | yes MS | no MS |
|---|---|---|
| Waist circumference cm | 97 ± 9.80 | 91 ± 8.6 * |
| BMI kg/m$^2$ [kg] | 29.3 ± 3.08 [82] | 27.9 ± 1.97 * [80] |
| Total cholesterol mg/dL | 220 ± 23.9 | 218 ± 23.9 |
| HDL cholesterol mg/dL | 37 ± 11.4 | 36 ± 5.8 |
| Triglycerides mg/dL | 213 ± 45.1 | 211 ± 53.8 |
| Glycemia mg/dL | 110 ± 11.1 | 103 ± 5.6 * |
| Mx arterial Blood pressure mm Hg | 128 ± 4.8 | 125 ± 3.3 * |
| Mn arterial Blood pressure mm Hg | 80 ± 8.8 | 74 ± 8.2 * |

MS = the metabolic syndrome according to ATP III 2005 criteria

Mx BP = Maximum arterial blood pressure

Mn BP = Minimum arterial blood pressure

* $p < 0.05$; t-test for independent data, comparison of yes MS with no MS.

For all patients treatment began with a dosage of 4 tbts/die (tablets/day) for a period of three months. Each tablet of the product contained 500 mg of a mixture composed of 91% chitosan (characteristics given in table 3), 6% ascorbic acid and 3% tartaric acid.

TABLE 3

Characteristics of chitosan

| Specifications | Characteristics |
|---|---|
| Appearance | Free flowing powder |
| Colour | From off-white to pale yellow |
| Odour | Odourless |
| Solution appearance | Clear, from colourless to pale yellow |
| Solubility (sol. in 1% acetic acid) | ≥80% |
| Degree of deacetylation | ≥70% |
| Viscosity (0.5% CTS, 0.0% Hac, 20° C.) | ≤100 nPa · s |
| Water | ≤10% |
| Ash | ≤1% |
| Proteins | Not determinable |
| pH | 6.0-9.0 |
| Mass density | ≥0.10 mg/ml |
| Particle size | ≥600 mesh |

For convenience, this composition was called polyglucosamine, or PG (a term used in all experimental trials on body weight and dyslipidemia under study and/or in print). The tablets were consumed to the extent of 2 tbts/meal with half a glass of water 30 minutes before main meals. Therefore the daily dosage was 2 g/day. The results are given in table 4.

TABLE 4

Comparison of parameters and differences between patients with and without MS after PG therapy

| Parameters | Yes MS | | No MS | | Difference after therapy | |
| | Before treatment | After treatment | Before treatment | After treatment | yes MS | no MS |
|---|---|---|---|---|---|---|
| Waist circumference (cm) | 97 ± 9.80 | 91 ± 9.6 * | 91 ± 8.6 | 87 ± 9.2 * | 8.8 ± 18.82 * | 6.4 ± 12.31 * |
| BMI (kg/m$^2$) | 29.3 ± 3.08 | 26.3 ± 6.18 * | 27.9 ± 1.97 | 25.4 ± 1.73 * | 3.0 ± 4.74 * | 2.2 ± 1.07 * |
| Total cholesterol (mg/dL) | 220 ± 23.9 | 190 ± 19.6 * | 218 ± 23.9 | 194 ± 20.7 * | 36 ± 38.1 * | 29 ± 31.9 * |
| HDL Cholesterol (mg/dL) | 37 ± 11.4 | 43 ± 7.3 * | 36 ± 5.8 | 45 ± 8.2 * | 4 ± 11.4 * | 8 ± 11.7 * |
| Triglycerides (mg/dL) | 213 ± 45.1 | 181 ± 21.5 * | 211 ± 53.8 | 170 ± 30.3 * | 39 ± 34.6 * | 45 ± 46.6 * |
| Glycemia (mg/dL) | 110 ± 11.1 | 93 ± 6.8 * | 103 ± 5.6 | 89 ± 6.7 * | 17 ± 10.7 * | 16 ± 13.9 * |
| Mx arterial blood pressure (mm Hg) | 128 ± 4.8 | 126 ± 5.2 * | 125 ± 3.3 | 124 ± 4.4 | 3 ± 4.5 * | 0 ± 2.1 * |
| Mn arterial blood pressure (mm Hg) | 80 ± 8.8 | 77 ± 9.0 * | 74 ± 8.2 | 74 ± 8.3 | 3 ± 8.2 * | 0 ± 2.7 * |

* $p < 0.05$; t-test for independent data.

The data presented show that the differences in effects between the two groups are not very substantial. The only clear difference can be seen in the treatment-induced action on both minimum and maximum arterial blood pressure.

As the MS is a multi-parametric entity, the averaged data presented tend to level out. In this respect, a hypertensive patient with raised glycemia and overweight is affected by MS (three of the 5 ATP III 2005 parameters are altered), as is a patient with normal blood pressure, raised glycemia, overweight and raised triglycerides (three of the 5 ATP III 2005 parameters, though different from the previous, are altered). This is the reason why the various parameters taken on average have a tendency to level out.

Example 2

Evaluating How Many Patients Recover from MS by Administration of Chitosan

In order to overcome the drawback of "levelling out" of the data in the studies described in example 1 and to determine the clinical validity of the therapy, patients with MS prior to treatment were isolated and it was then determined how many of these "recovered" from MS after treatment.

Based on this criterion, of the 27 cases affected by MS, no less than 16 were found to have recovered from MS after three months' treatment with the product under examination.

Therefore, it has been surprisingly established that the product is effective in 59% of cases and that the key elements, determined from these "recoveries" from MS, are reduction of glucose levels and reduction of arterial BP. In conclusion, this trial indicates that treatment with the chitosan-based PG product is effective in comprehensive therapeutic treatment and comprehensive prevention of the metabolic syndrome.

The invention claimed is:

1. A method for comprehensive therapeutic treatment of metabolic syndrome comprising:

(a) identifying a patient as suffering from metabolic syndrome wherein at least three of the following parameters are positively assessed in said patient:

(i) waist circumference equal to or greater than 102 cm in men and equal to or greater than 88 cm in women, (ii) triglyceride level equal to or greater than 150 mg/dL, (iii) HDL cholesterol level less than 40mg/dL in men and less than 50 mg/dL in women, (iv) arterial blood pressure equal to or greater than 130/85 mm Hg, and
(v) elevated basal fasting glucose equal to or greater than 100 mg/dL; and
(b) administering to said patient suffering from metabolic syndrome a composition consisting essentially of chitosan, ascorbic acid and tartaric acid, wherein the ascorbic acid is in an amount between 1 and 10%, by weight based on the amount of the chitosan and said administering is carried out at a dosage effective to modify at least two of the three positively assessed parameters in the patient in the absence of dietary modification by said patient as follows:
(i) a waist circumference of less than 102 cm in men and less than 88 cm in women,
(ii) a triglyceride level of less than 150 mg/dL,
(iii) an HDL cholesterol level of equal to or greater than 40 mg/dL in men and equal to or greater than 50 mg/dL in women,
(iv) an arterial blood pressure of less than 130/85 mm Hg, and
(v) a non-elevated basal fasting glucose of less than 100 mg/dL.

2. The method as claimed in claim 1, wherein one of the said parameters positively assessed is parameter (v) and said administering is carried out at a dosage effective to modify parameter (v) to achieve a non-elevated basal fasting glucose of less than 100 mg/dL.

3. The method as claimed in claim 1, wherein two of the said parameters positively assessed are the parameters (iv) and (v).

4. The method as claimed in claim 1, wherein the composition further comprises lubricants and/or excipients and/or adjuvants and/or flavourings and/or antioxidants.

5. The method as claimed in claim 1, wherein the lubricant is magnesium stearate.

6. The method as claimed in claim 1, wherein ascorbic acid is present in quantities between 4% and 8% by weight with respect to chitosan.

7. The method as claimed in claim 1, wherein the composition is administered in the form of a tablet.

8. The method as claimed in claim 1, wherein the composition is administered in an amount containing from 0.1 g to 1.5 g of chitosan.

9. The method as claimed in claim 1, wherein the composition is administered in an amount containing from 0.25 g to 1 g of chitosan.

10. The method as claimed in claim 1, wherein the composition is administered in an amount containing from 400 mg to 600 mg of chitosan.

* * * * *